United States Patent [19]

Francis

[11] Patent Number: 5,695,748
[45] Date of Patent: Dec. 9, 1997

[54] COMPOSITION AND PROCESS FOR THE TREATMENT AND RESTORATION OF HAIR

[76] Inventor: Sabina Francis, 814 Tilden St., Bldg. B, Apt.3 A, Bronx, N.Y. 10467

[21] Appl. No.: 540,892

[22] Filed: Oct. 11, 1995

[51] Int. Cl.$^6$ ................... A61K 7/00; A61K 7/06
[52] U.S. Cl. ............... 424/74; 424/70.1; 424/195.1
[58] Field of Search ............. 424/74, 70.1, 195.1

[56] References Cited

U.S. PATENT DOCUMENTS

| | | | |
|---|---|---|---|
| 2,551 | 4/1842 | Clirehugh . | |
| 51,319 | 12/1865 | Howard . | |
| 75,806 | 3/1868 | Stearns . | |
| 83,440 | 10/1868 | Atwood . | |
| 112,632 | 3/1871 | Reybert . | |
| 112,749 | 3/1871 | Thomas et al. . | |
| 129,608 | 7/1872 | Smith . | |
| 285,045 | 7/1883 | Leip | 424/74 |
| 289,922 | 12/1883 | Miles | 424/74 |
| 328,631 | 10/1885 | Allen | 424/74 |
| 386,617 | 7/1888 | Wallace . | |
| 604,111 | 5/1898 | Edwards . | |
| 3,824,304 | 7/1974 | Villanueva . | |
| 4,511,555 | 4/1985 | Faust | 424/74 |
| 4,658,839 | 4/1987 | Dallal et al. | 132/7 |
| 4,849,214 | 7/1989 | Ruiseco | 424/74 |
| 4,880,621 | 11/1989 | Grollier et al. | 424/74 |
| 4,904,471 | 2/1990 | Jones | 424/195.1 |
| 5,215,760 | 6/1993 | Kavoussi et al. | 424/74 |
| 5,217,711 | 6/1993 | De Oliveira | 424/70 |
| 5,407,675 | 4/1995 | Eternad-Moghadam | 424/401 |
| 5,427,776 | 6/1995 | Isnard | 424/70.1 |

FOREIGN PATENT DOCUMENTS

| | | | |
|---|---|---|---|
| 051789 | 5/1982 | European Pat. Off. | 424/74 |
| 104265 | 3/1917 | United Kingdom | 424/74 |

*Primary Examiner*—Sallie M. Gardner
*Attorney, Agent, or Firm*—Abelman, Frayne & Schwab

[57] ABSTRACT

A multi-stage process, employing novel compositions or mixtures of ingredients, for the therapeutic conditioning of damaged or thinning human hair and for promoting the growth and restoration of hair which has been lost, which includes a cleansing stage, a treatment stage and a heating stage.

21 Claims, No Drawings

COMPOSITION AND PROCESS FOR THE TREATMENT AND RESTORATION OF HAIR

BACKGROUND OF THE INVENTION

This invention relates to a hair treatment process and composition and, more specifically, to a process and composition for providing enhanced fullness and body to human hair, to conditioning the hair, and to treating and restoring damaged, thinning and lost human hair.

In the recorded literature, whether medical, literary, or patent, the trials and tribulations associated with hair loss, diminished hair, poor hair quality, hair restoration and other problems associated with the hair have been recounted many times, oftentimes, with anguish and travail. Some of these problems are attributable to the disease process, be it physical or emotional, while others are attributable to a genetic pre-disposition, such as male pattern baldness. Many remedies have been proposed to restore hair and provide fullness and sheen to damaged hair, to prevent the thinning or loss of hair, to nourish the underlying scalp and its hair follicles so as to promote or improve hair growth, and to provide therapy to hair which has been damaged by external causes, whether by the elements, by excessive and damaging manipulation, or due to systemic illnesses.

Most of these proposed remedies or therapies whether they be found in the scientific, patent or popular literature have met with varying degrees of success; ranging from outright failure for the most part to drugs such as Rogaine® (minoxidil) which has been approved by the Food and Drug Administration for promoting hair growth. Rogaine, which must be administered pursuant to a physicians prescription, has met with a limited degree of success in promoting hair growth and has caused at least some of its users to suffer from certain adverse reactions to their scalps. In addition, it must be used on a continuing basis, there can be no cessation in its use, and it is an expensive prescription medicine.

Thus, people with thinning hair, hair which has been damaged due to a disease state or due to external causes, or any other derangement in the natural hair growth process, have, to all intents and purposes, been met with an impasse when seeking to alleviate or ameliorate their hair problems, whether by the use of prescription medicines, over-the-counter medicines, herbal medicines, or a variety of other therapies, such as, for example, hair implants, which are costly and time-consuming, and which oftentimes produces indifferent results, or no results at all.

Accordingly, it is an object of the present invention to provide a hair conditioning therapy composition which employs naturally occurring ingredients which are compatible with the hair and the scalp and which have few or no adverse side effects.

It is another object of the present invention to provide a composition, and a process for employing said composition, which serves to ameliorate various problems associated with human hair.

It is still another object of the present invention to provide a multi-stage process and novel compositions for use with certain stages of said process to ameliorate and improve various problems associated with the treatment and care of human hair, including the restoration and regrowth of lost or thinning hair, conditioning and enhancing damaged hair and treating other hair and scalp disorders.

Other objects, advantages and features of the present invention will become apparent through a reading of the following more detailed description of the invention.

SUMMARY OF THE INVENTION

The present invention is directed to a multi-stage process, employing novel compositions or mixtures of natural ingredients during certain stages of the process, which unexpectedly has proven effective for providing therapeutic conditioning to damaged or thinning human hair and for promoting hair restoration, growth and thickness. These compositions or mixtures of ingredients are all substantially naturally occurring materials and, as such, provide natural nutrients for the hair and scalp without adverse effects thereto as may occur with the use of synthetic organic and/or inorganic compounds.

In the first stage or step of the process, which is referred to herein as the cleansing step or stage, the same or differing quantities of three naturally occurring ingredients are applied topically to the hair and scalp as a mixture to provide a thorough and complete cleansing.

In the second step or stage of the process, which is referred to herein as the application and/or treatment stage, the same or differing quantities of three (3) different naturally occurring oils and one non-oil based product are topically applied to the hair and scalp as a mixture.

After the application or treatment stage, in the next or third stage, the hair is heated at an elevated temperature for a sufficient period of time to allow the mixture applied in the application or treatment stage, namely, the second stage, to condition the hair and the scalp with the oils by promoting penetration via the heating process.

Subsequent to heating at an elevated temperature, the hair which is now in a greasy state is shampooed with a conventional over-the-counter shampoo and the hair is then styled by means of conventional styling equipment, such as hair blowers, brushes, combs, etc.

While it is not absolutely necessary, it is preferred and recommended that the man or woman undergoing the hair treatment therapy outlined above, also treat his or her hair at home, between weekly visits to the cosmetologist or hair care professional in the salon where the cleansing step and the application/treatment step are performed. This step is referred to as the after-care treatment step or stage, which is an optional stage, and involves the topical application to the hair and scalp, preferably at nighttime before going to bed, of the same or differing quantities of two ingredients in the form of a liquid. While it is preferred that this after-care or home treatment be done once each night between salon visits, it could also be done once every other night, or once every third, fourth, fifth or even sixth night, depending upon the condition being treated and the individual's willingness to accept and undergo the complete hair therapy regimen.

A fairly typical regimen for treatment of thinning or damaged hair would involve weekly visits to the salon for at least eight weeks, the person would have their hair cleansed in the first stage and treated in the second stage. At the end of eight (8) weeks, the subjects treated in accordance with the foregoing regimen noted improvements in the state of their hair, such as improved conditioning and/or fullness. In certain instances, after a period of six (6) months a significant increase in hair growth was noted in those scalp areas from which the hair had previously receded.

While it is not known with any degree of certainty as to how the therapeutic process of the present invention functions, it is hypothesized that the mixture of ingredients used in the cleansing stage and in the application or treatment stage, as well as the ingredients used in the after-care stage, serve to unblock previously blocked hair follicles, restore the follicles to a healthy state and continue to maintain their health, as well as providing strength to existing or newly grown hair shafts by virtue of the natural nutrients which are used in each stage of the hair therapy process.

DETAILED DESCRIPTION OF THE INVENTION

In the first stage or step of the invention, also referred to as the cleansing stage, a liquid cleansing mixture or composition comprising sage, in the form of either a powder or a tea; aloe, preferably in the form of a powder, but alternatively in the form of an oil or a gel; and nettles, which is a naturally occurring leaf and which is known to be a topically active mild epidermal stimulant, and which can be used in the form of a tea or powder, is applied as a substantially homogeneous mixture or composition to the scalp and the hair and thoroughly massaged therein, and is allowed to remain on the hair or scalp for a period of from about 1 minute to about 60 minutes, or possibly longer, with a period from about 5 minutes to about 30 minutes being preferred, and with a period from about 5 minutes to about 15 minutes being especially preferred. The quantities of ingredients employed can each be the same, or differing quantities, by weight, of each ingredient can be used. While from about 0.1 ounces to about 5.0 ounces of each ingredient can be employed, it is preferred to employ from about 0.5 ounces to about 3.0 ounces of each ingredient, with about 1.0 ounce of each ingredient being especially preferred. All weights referred to herein are fluid weights. The cleansing liquid mixture, is thereafter, removed by rinsing with water.

In the second or following stage or step of the process, which is also referred to as the treatment or application stage, a mixture of four ingredients is applied to the scalp, the remaining hair, or the damaged hair.

The treatment composition or mixture includes castor oil; shea butter, which is a butter derived from the African cocoa bean; wheat germ oil; and white iodine.

The quantities of the ingredients employed can each be the same, or differing quantities of each ingredient can be employed.

While the composition or mixture can contain from about 0.1 ounces to about 5.0 ounces of each of the foregoing ingredients in the mixture, it is preferred to employ from about 0.5 ounces to about 3.0 ounces, with 1 ounce of each of the ingredients being especially preferred.

The four ingredients are mixed together and then shaken until they are substantially homogeneous in consistency, and they are thereafter applied to the scalp and hair by manually massaging, or by means of a implement such as, for example, a suitable brush.

After the application stage is complete, the hair or scalp which is now in a greasy state is heated at an elevated temperature in the third stage by means of, for example, a hair dryer, of a type which is typically found in a beauty salon. While such a professional dryer is preferred, other heating means can be employed, as, for example, a hand-held dryer.

When a professional dryer is employed, it is placed over the head of the subject having the treatment stage ingredients on the hair and scalp, and is maintained there for a period of from about 15 minutes to about 60 minutes at either the medium setting or the high setting. The preferred residence time is from about 30 minutes to about 45 minutes, which has been shown to be the preferred time range for achieving the best results.

Thereafter, the hair which is in a greasy and oily state is shampooed with a conventional over-the-counter type shampoo, which is preferably non-medicated, but which can medicated if dictated by the nature of the subject's hair or scalp problem or disorder. Thereafter, the hair is styled by the use of typical hair styling equipment.

The so-called after-care stage of the process is optional. It is, however, preferred and recommended from the standpoint of producing improved results within a shorter period of time. Thus, a man or woman undergoing the previously described hair treatment therapy is provided with an after-care treatment liquid, which is to be employed preferably at home between weekly visits to the salon. The after-care treatment mixture or composition includes Indian hemp, which is a powdered form of a root or leaf, which has been mixed together with aloe oil. The quantities of ingredients employed can each be the same, or differing quantities of each ingredient can be employed. The composition or mixture can employ from about 0.1 ounce to about 5.0 ounces of each ingredient. It is preferred, however, to employ from about 0.5 ounces to about 3.0 ounces, with about 1.0 ounce of each ingredient being especially preferred. While it is preferred that this after-care or home treatment be applied each night between visits to the salon, it can also be done once every other night, or once every third night, or even once every fourth, fifth or sixth night, depending upon the condition being treated and the individual's willingness to undertake the complete hair therapy regimen. The after-care composition is shaken thoroughly to insure a uniform dispersion and applied to the scalp by manually massaging the same into the hair and scalp and allowing it to remain thereon overnight.

In order to disclose more clearly the nature of the present invention, the following examples illustrating the invention are given. It should be understood, however, that this is done solely by way of example and is intended neither to delineate the scope of the invention nor limit the ambit of the appended claims.

EXAMPLE 1

In each of the examples set forth below, a first cleansing stage was employed. The liquid cleansing mixture or composition was a homogeneous mixture containing one ounce of sage, one ounce of aloe and one ounce of nettles.

This homogeneous mixture or composition was massaged thoroughly into the hair and the scalp and was allowed to remain thereon for a period of about ten minutes. Thereafter, the liquid cleanser was removed from the hair and scalp by rinsing with water.

Subsequently, in each of the examples below a treatment stage was employed comprising a homogeneous mixture of one ounce of castor oil, one ounce of shea butter, one ounce of wheat germ oil and one ounce of white iodine was applied to the hair and scalp by thoroughly massaging it into the hair or scalp, which was in a greasy state following the application of the foregoing mixture. The hair was then dried for a period of about thirty minutes using a professional hair dryer set either at the medium setting or at the high setting. The temperature setting is dependent upon the ability of the subject to withstand the higher temperatures found at the high setting.

Upon completion of the drying step, the hair was then shampooed with a conventional shampoo and was then blown and styled with appropriate hair styling equipment.

In each of the examples which follow, the client applied on a nightly basis an after-care treatment liquid, which consists of a liquid mixture containing one ounce of Indian hemp and one ounce of aloe oil. The after-care composition was shaken thoroughly to ensure a uniform dispersion and applied to the hair and scalp by manually massaging the same into the hair and the scalp and allowing it to remain thereon overnight.

EXAMPLE 2

A middle-aged female subject whose hair had been over-processed by permanents, damaged by weaving, as well as having lost hair around the front left edge of her scalp due to glass damage sustained in an automobile accident, was treated in accordance with the method as described in Example 1 above for a period of about five months. As a result of following the method or regimen outlined in Example 1, the subject's hair, which was lost due to the accident, was restored; when both doctors and nurses had said it could not be restored, and, in addition, the subject's hair is now strong and healthy looking, and is no longer breaking off, but is continually growing.

As a result of undergoing the treatment described in Example 1, the subject's hair has grown in length so that it can now be styled, whereas previously the hair could not even be curled with the smallest available curling iron.

EXAMPLE 3

A middle-aged female subject suffering from thinning hair and also a bald spot in the center of her head which had enlarged considerably from the time she first noticed it. In addition, the hair at the sides and nape of her head were also disappearing.

Upon an initial consultation with a dermatologist, the subject was diagnosed as having a form of alopecia which the dermatologist determined was probably due to the overuse or improper use of chemicals, including hair relaxers. The dermatologist also stated the hair loss was also probably due to stress, improper nutrition, and a series of medical operations which the subject had undergone. The dermatologist prescribed a prescription medicine, minoxidil, for a period of six months. As a result of the use of this prescription medication, the subject developed many negative side effects, such as itching, skin rash, burning of the scalp, reddening of the scalp and abrasions to the surface of the scalp.

Thereafter, the subject discontinued the medicine and followed the treatment regimen or method described in Example 1 above for five months. After the initial treatment, the subject's hair was softer and there was no breakage of the hair. After each subsequent treatment, the subject's hair began to feel stronger and grew thicker, without any loss of hair. As the series of treatments progressed, the subject's hair began to fill-in in the previously balding and thinning areas and the subject had achieved a significant degree of improvement after a complete set of treatments.

As a result of employing the composition and following the method set forth in Example 1 above, the subject's hair has nearly attained the length desired, as well as the thickness sought to be achieved.

EXAMPLE 4

A middle-aged female subject was losing her hair in various locations, at both the front and top of her head for a period of over a year. The subject had gone to many 5 physicians and used various medications, none of which were of any avail in helping restore the bald or denuded spots at the top and at the front of her scalp.

In a four month period during which she underwent the treatment method using the mixtures set forth in Example 1, the growth of hair has recommenced. The denuded spots or bald areas in the front of the scalp have filled-in completely and there has been a partial filling-in and restoration of the bald spot on the top of the subject's head.

EXAMPLE 5

A middle-aged female subject had a bald spot in the center of her head and also down the right side of her head. Her hair was so short that it had to be set with end papers laid on some parts of her hair due to the shortness of the hair.

Employing the method and compositions set forth in Example 1, the subject noticed a significant improvement in the texture of her hair and the hair ceased falling out. After each subsequent treatment, the subject noticed improved results.

After an initial eight week course of treatment, followed by a second eight week course of treatment, the subject's hair has progressed so that the previous bald areas have filled-in, the texture of the hair has improved significantly and the subject no longer has the need to use end papers to style her hair, but can now use large hair rollers to style her hair.

EXAMPLE 6

A middle-aged male subject suffering from baldness and thinning of the hair in the frontal and middle sections of the scalp undertook the regimen set forth in Example 1.

After each successive visit the subject noted that additional hair had grown in the bald or denuded sections and after five months of treatment the subject now has fifty percent more hair in both the frontal and middle sections of his scalp.

While only certain embodiments have been disclosed, it will be apparent to those skilled in the art that various modifications can be made without departing from the spirit and scope of the present invention. All such modifications coming within the scope of the appended claims are intended to be carried out thereby.

What is claimed is:

1. A process for conditioning damaged, thinning hair and for restoring hair growth which comprises the steps of:
    (a) applying a cleansing mixture of sage, aloe and nettles to the hair and scalp in an amount and for a period of time sufficient to effect cleansing and then removing same;
    (b) applying a treatment mixture of castor oil, shea butter, wheat germ oil and white iodine to the hair and scalp in an amount and for a period of time effective to treat the hair and scalp; and
    (c) heating the treatment mixture on the hair and scalp for a period of time sufficient to promote penetration of the treatment mixture into the hair and scalp and then removing the treatment mixture.

2. The process of claim 1 wherein in step (a) quantities, by weight, of sage, aloe and nettles employed differ from each other.

3. The process of claim 1 wherein in step (a) the quantities, by weight, of sage, aloe and nettles employed are the same as each other.

4. The process of claim 1 wherein in the cleansing mixture of step (a) from about 0.5 to about 3.0 ounces of sage is employed, from about 0.5 to about 3.0 ounces of aloe is employed and from about 0.5 to about 3.0 ounces of nettles is employed.

5. The process of claim 4 wherein the quantities of sage, aloe and nettles are each about one ounce.

6. The process of claim 1 wherein the cleansing mixture of step (a) is applied to the hair and scalp for a period of from about 1 minute to about 20 minutes.

7. The process of claim 6 wherein the cleansing mixture of step (a) is applied to the hair and scalp for a period of from about 5 to about 10 minutes.

8. The process of claim 1 wherein in the treatment mixture of step (b) differing quantities, by weight, if castor oil, shea butter, wheat germ oil and white iodine are employed.

9. The process of claim 1 wherein in the treatment mixture of step (b) the same quantities, by weight, of castor oil, shea butter, wheat germ oil and white iodine are employed.

10. The process of claim 1 wherein in the treatment mixture of step (b) from about 0.5 ounces to about 3.0 ounces, respectively, of castor oil, shea butter, wheat germ oil and white iodine are employed.

11. The process of claim 10 wherein in step (b) the quantities of castor oil, shea butter, wheat germ oil and white iodine are each about one ounce.

12. The process of claim 1 wherein the treatment mixture of step (b) is applied to the hair and scalp for a period of from about 15 minutes to about 60 minutes.

13. The process of claim 12 wherein the treatment mixture of step (b) is applied to the hair and scalp for a period of from about 30 minutes to about 45 minutes.

14. The process of claim 1 wherein the hair and scalp is treated at least once each week.

15. The process of claim 14 wherein the period of treatment is at least about eight weeks.

16. The process of claim 1 and further including the application of an after-care treatment mixture to the hair and scalp comprising aloe and Indian hemp.

17. The process of claim 16 wherein the mixture is a liquid.

18. The process of claim 16 wherein the aloe is in the form of an oil.

19. The process of claim 16 wherein the Indian hemp is in the form of a powder.

20. The process of claim 16 wherein the after-care treatment mixture is applied nightly for at least eight weeks.

21. The process of claim 16 wherein the after-care treatment is applied for a period of from about one night per week to about seven nights per week for from about one week to about eight weeks.

* * * * *